US010426612B2

(12) United States Patent
Costello

(10) Patent No.: US 10,426,612 B2
(45) Date of Patent: Oct. 1, 2019

(54) MEDICAL DEVICE DELIVERY SYSTEMS AND METHODS

(71) Applicant: Medtronic Vascular Galway, Ballybrit, Galway (IE)

(72) Inventor: Declan Costello, Ballybrit (IE)

(73) Assignee: Medtronic Vascular Galway, Ballybrit, Galway (IE)

( * ) Notice: Subject to any disclaimer, the term of this patent is extended or adjusted under 35 U.S.C. 154(b) by 413 days.

(21) Appl. No.: 15/181,463

(22) Filed: Jun. 14, 2016

(65) Prior Publication Data

US 2016/0361164 A1 Dec. 15, 2016

Related U.S. Application Data

(63) Continuation of application No. 14/038,195, filed on Sep. 26, 2013, now Pat. No. 9,387,074.

(51) Int. Cl.
*A61F 2/24* (2006.01)
*A61F 2/95* (2013.01)

(52) U.S. Cl.
CPC .............. *A61F 2/2427* (2013.01); *A61F 2/95* (2013.01); *A61F 2002/9505* (2013.01); *Y10T 29/49925* (2015.01)

(58) Field of Classification Search
CPC .. A61F 2/24; A61F 2/2427; A61F 2/95; A61F 2002/9505; A61F 2/2436; A61F 2/2439; A61F 2002/9522; A61F 2/962; A61F 2002/9665; A61F 2/966; A61F 2/00; A61F 2/07; A61F 2/04; A61F 2/0022; Y10T 29/49925

USPC ......................................................... 623/2.11
See application file for complete search history.

(56) References Cited

U.S. PATENT DOCUMENTS

| 7,329,279 | B2 | 2/2008 | Haug et al. |
| 7,837,727 | B2 | 11/2010 | Goetz et al. |
| 8,052,732 | B2 | 11/2011 | Mitchell et al. |
| 8,241,344 | B2 | 8/2012 | Kuslelka |
| 2008/0262592 | A1* | 10/2008 | Jordan ...................... A61F 2/95 623/1.11 |
| 2009/0287290 | A1 | 11/2009 | Macaulay et al. |
| 2010/0049313 | A1 | 2/2010 | Alon et al. |
| 2010/0100167 | A1* | 4/2010 | Bortlein ................ A61F 2/2436 623/1.11 |
| 2011/0098805 | A1 | 4/2011 | Dwork et al. |
| 2011/0251675 | A1 | 10/2011 | Dwork |
| 2011/0264203 | A1 | 10/2011 | Dwork et al. |
| 2011/0295216 | A1 | 12/2011 | Miller |

(Continued)

*Primary Examiner* — George J Ulsh
(74) *Attorney, Agent, or Firm* — Medler Ferro Woodhouse & Mills PLLC

(57) ABSTRACT

A delivery system for deploying a medical device includes a first attachment member configured to selectively couple to and radially constrain a first end portion of the medical device. The delivery system also includes a second attachment member configured to selectively couple to and radially constrain a second end portion of the medical device. The first attachment member is configured to move relative to the second attachment member such that the first attachment member applies a first tensile force to the first end portion of a medical device in a first direction and the second attachment member applies a second tensile force to the second end portion of a medical device in a second direction substantially opposite from the first direction.

12 Claims, 9 Drawing Sheets

(56) References Cited

U.S. PATENT DOCUMENTS

2012/0185036 A1\* 7/2012 Arnault De La Menardiere ........ A61F 2/954 623/1.35
2016/0120676 A1\* 5/2016 Gomes Nogueira ..... A61F 2/95 623/1.11

\* cited by examiner

MEDICAL DEVICE DELIVERY SYSTEMS AND METHODS

RELATED APPLICATIONS

This application is a Continuation of and claims the benefit of U.S. patent application Ser. No. 14/038,195 filed Sep. 26, 2013, now allowed. The disclosures of which are herein incorporated by reference in their entirety.

BACKGROUND

Field

Embodiments of the invention relate to systems and methods for loading an implantable medical device onto a delivery device and, particularly, to systems and methods for loading a valve prosthesis onto a delivery catheter.

Background

Patients suffering from valve regurgitation or stenotic calcification of the leaflets can be treated with a heart valve replacement procedure. A traditional surgical valve replacement procedure requires a sternotomy and a cardiopulmonary bypass, which creates significant patient trauma and discomfort. Traditional surgical valve procedures can also require extensive recuperation times and may result in life-threatening complications.

One alternative to a traditional surgical valve replacement procedure is delivering the replacement heart valve prosthesis using minimally-invasive techniques. For example, a heart valve prosthesis can be percutaneously and transluminally delivered to an implantation location. In such methods, a heart valve prosthesis can be compressed or crimped on a delivery catheter for insertion within a patient's vasculature; advanced to the implantation location; and re-expanded to be deployed at the implantation location. For example, a catheter loaded with a compressed heart valve prosthesis can be introduced through an opening in the femoral artery and advanced through the aorta to the heart. At the heart, the prosthesis can be re-expanded to be deployed at the aortic valve annulus, for example.

BRIEF SUMMARY

In some embodiments, a delivery system for deploying a medical device includes a first attachment member configured to selectively couple to and radially constrain a first end portion of the medical device, and a second attachment member configured to selectively couple to and radially constrain a second end portion of the medical device opposite the first end portion. The first attachment member can be configured to move relative to the second attachment member such that the first attachment member applies a first tensile force to the first end portion of a medical device in a first direction and the second attachment member applies a second tensile force to the second end portion of a medical device in a second direction substantially opposite from the first direction.

In some embodiments, a method of deploying a medical device includes coupling a first end portion of the medical device to a first attachment member of a delivery system. The method also includes coupling a second end portion of the medical device to a second attachment member of the delivery system. Further, the method includes moving the first attachment member relative to the second attachment member to increase a distance between the first attachment member and the second attachment member. Moving the first attachment member relative to the second attachment member causes the first attachment member to apply a first tensile force to the first end portion of the medical device in a first direction and the second attachment member to apply a second tensile force to the second end portion of the medical valve in a second direction substantially opposite from the first direction, whereby the medical device is compressed.

A system for replacing a native heart valve of a patient includes a prosthetic heart valve and a delivery system for deploying the prosthetic heart valve. The prosthetic heart valve includes a frame and a valve assembly coupled to the frame. The frame includes a first end portion, an intermediate portion, and a second end portion. The delivery system includes a first attachment member configured to selectively couple to and radially constrain a first end portion of the prosthetic heart valve. The delivery system also includes a second attachment member configured to selectively couple to and radially constrain a second end portion of the prosthetic heart valve. The first attachment member can be configured to move relative to the second attachment member such that the first attachment member applies a first tensile force to the first end portion of the prosthetic heart valve in a first direction and the second attachment member applies a second tensile force to the second end portion of the prosthetic heart valve in a second direction substantially opposite from the first direction.

Further features and advantages of the embodiments, as well as the structure and operation of various embodiments, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

The accompanying drawings, which are incorporated herein and form part of the specification, illustrate the embodiments and, together with the description, further serve to explain the principles of the embodiments and to enable a person skilled in the relevant art(s) to make and use the embodiments.

Figure 1:
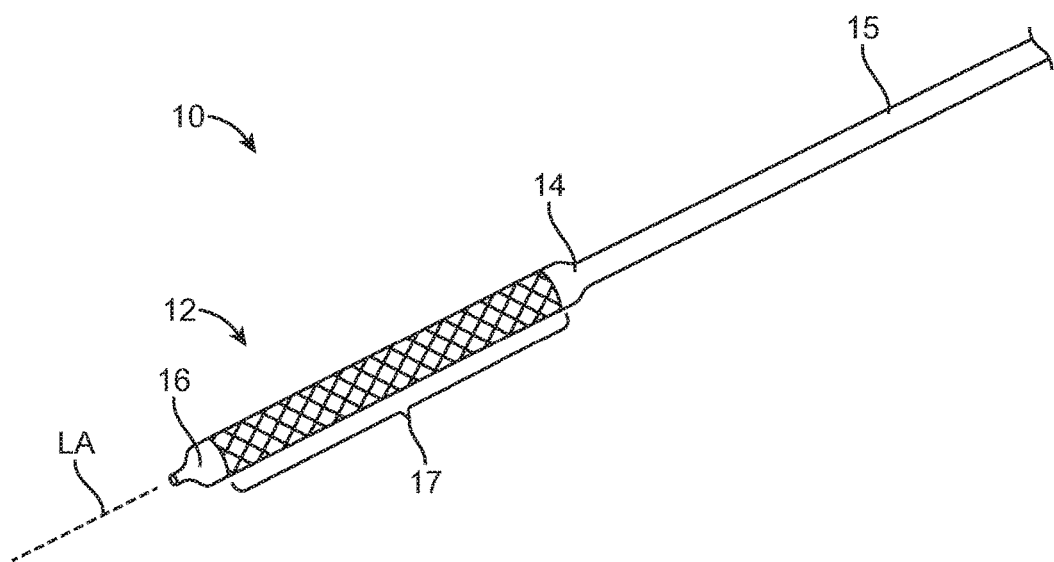
FIG. 1 illustrates a perspective view of a delivery system according to an embodiment.

The features and advantages of the embodiments will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

The embodiments described, and references in the specification to "one embodiment," "an embodiment," "an example embodiment," "some embodiments," etc., indicate that the embodiments described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that such feature, structure, or characteristic can be used in connection with other embodiments whether or not explicitly described.

FIG. 1 illustrates a perspective view of a delivery system 10 having a longitudinal axis LA according to an embodiment. Delivery system 10 can be configured to deliver a medical device 12 to an implantation location within a patient's body.

Figure 6:
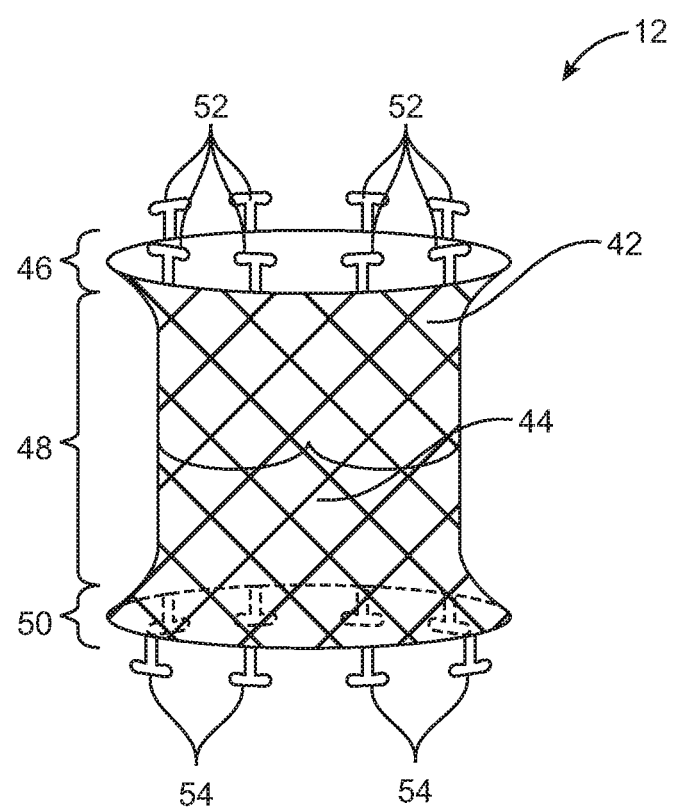
FIG. 6 is a perspective view of a medical device for use with a delivery system according to an embodiment.

In some embodiments, medical device 12 is a valve prosthesis, a stent, or any other suitable collapsible medical device. For example, medical device 12 can be a valve prosthesis as shown in FIG. 6. Referring to FIG. 6, medical device 12 is a valve prosthesis that comprises a collapsible and expandable frame 42 and a valve assembly 44 coupled to the frame. Frame 42 comprises a first end portion 46, for example, an outflow portion of valve prosthesis 12; an intermediate portion 48; and a second end portion 50, for example, an inflow end of valve prosthesis 12. In some embodiments, first end portion 46 comprises one or more coupling members 52. In some embodiments, second end portion 50 comprises one or more coupling members 54. For example, coupling members 52 and 54 can have a paddle shape, an eyelet shape, a T-shape, or any other suitable shape for coupling medical device 12 to delivery system 10. Medical device 12 can be self-expanding.

Referring back to FIG. 1, delivery system 10 comprises a first attachment member 14, for example, a spindle, configured to selectively couple to medical device 12 such that relative axial movement between first attachment member 14 and medical device 12 at the point of coupling (for example, at first end portion 46) is substantially prevented. Delivery system 10 also comprises a second attachment member 16, for example, a spindle, configured to selectively couple to medical device 12 such that relative axial movement between second attachment member 16 and medical device 12 at the point of coupling (for example, at second end portion 46) is substantially prevented. As shown in FIG. 1, second attachment member 16 is distal to first attachment member 14.

Delivery system 10 can be configured such that first attachment member 14 is axially movable relative to second attachment member 16 so that an axial distance 17 between attachment members 14 and 16 changes as first attachment member 14 moves relative to second attachment member 16. In some embodiments, delivery system 10 can be configured such that as first attachment member 14 moves relative to second attachment member 16 to increase distance 17 between first and second attachment members 14 and 16, first attachment member 14 applies a first tensile force to medical device 12 in a first direction, for example, in a proximal direction parallel to longitudinal axis LA, and second attachment member 16 applies a second tensile force to medical device 12 in a second direction substantially opposite from the first direction, for example, a distal direction parallel to longitudinal axis LA. Applying the first and second tensile forces compresses—reduces an outer dimension—at least a portion or, in some embodiments, substantially all of medical device 12. Such compression of medical device 12 facilities delivery of medical device 12 through a patient's body lumens and cavities by decreasing the outer dimension of medical device 12.

In some embodiments, first attachment member 14 applies the first tensile force directly to coupling members 52 of medical device 12. In some embodiments, first attachment member 14 applies the first tensile force directly to a radially intermediate surface—a surface between the outer surface and the inner surface—of coupling members 52. In some embodiments, first attachment member 14 applies the first tensile force directly to an axially intermediate surface—a surface between the axial ends—of medical device 12. In some embodiments, second attachment member 16 applies the second tensile force directly to coupling members 54 of medical device 12. In some embodiments, second attachment member 14 directly applies the second tensile force to a radially intermediate surface—a surface between the outer surface and the inner surface—of coupling members 54. In some embodiments, second attachment member 16 applies the second tensile force directly to an axially intermediate surface—a surface between the axial ends—of medical device 12. In some embodiments, the first and second tensile forces are substantially coaxial. In some embodiments, the first and second tensile forces are substantially parallel to the longitudinal axis of the delivery system 10.

In some embodiments, first and second attachment members 14 and 16 can be spindles or any other suitable attachment structures.

In some embodiments, delivery system 10 comprises an outer shaft 15 that encompasses an inner shaft 26. Inner shaft 26 is movable relative to outer shaft 15. In some embodiments, first attachment member 14 is fixed relative to outer shaft 15—first attachment member 14 moves with outer shaft 15. In some embodiments, first attachment member 14 is integral with outer shaft 15. In some embodiments, first attachment member 14 is a discrete component from outer shaft 15. In some embodiments, second attachment member 16 is fixed relative to inner shaft 26—second attachment member 16 moves with inner shaft 26. In some embodiments, second attachment member 16 is integral with inner shaft 26. In some embodiments, second attachment member 16 is a discrete component coupled to a distal end of inner shaft 26.

In some embodiments, first attachment member 14 can be configured to selectively and radially constrain at least a portion of medical device 12, for example, first end portion 46, once medical device 12 is coupled to first attachment member 14. In such embodiments, first attachment member 14 substantially and selectively prevents outward radially expansion of first end portion 46 of medical device 12. In some embodiments, when first attachment member 14 and second attachment member 16 apply the first and second tensile forces to compress medical device 12, first attachment member 14 and second attachment member 16 can also radially restrain respective portions of medical device 12.

In some embodiments, second attachment member 16 can be configured to selectively and radially constrain at least a portion of medical device 12, for example, second end portion 50, once medical device 12 is coupled to second attachment member 16. In such embodiments, second attachment member 16 substantially and selectively prevents outward radially expansion of second end portion 50 of medical device 12.

In some embodiments, outward radially expansion of intermediate portion 48 of medical device 12 is substantially and selective prevented by the application of the first and second tensile force by first attachment member 14 and second attachment member 16, respectively.

In some embodiments, delivery system 10 does not include a capsule, minimizing the outer dimension of the delivery system.

Figure 2:
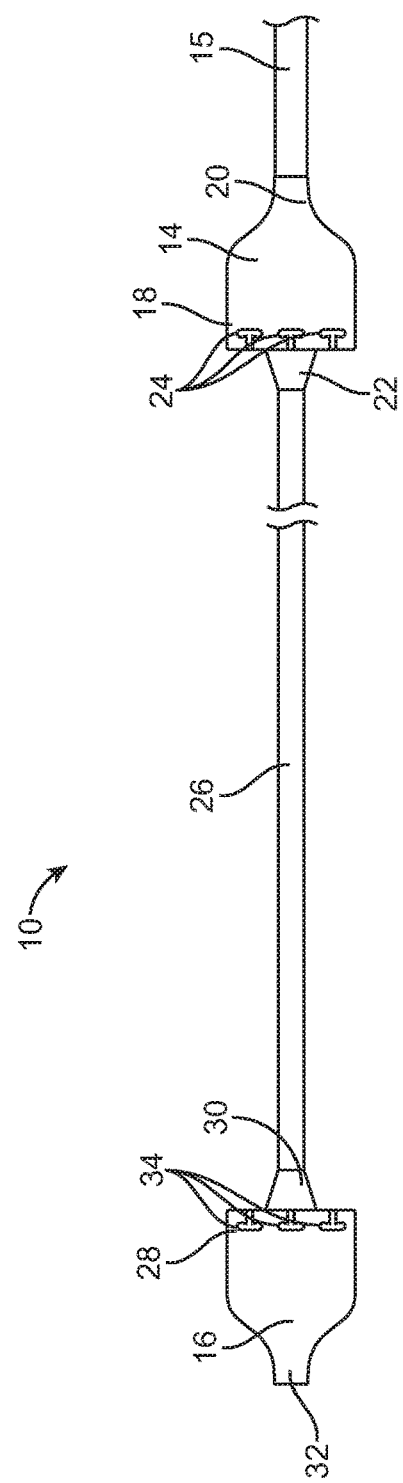
FIG. 2 illustrates a side view of first and second attachment members of a delivery system according to an embodiment.

FIG. 2 illustrates a side view of outer shaft 15, first attachment member 14, inner shaft 26, and second attachment member 16 according to an embodiment. Inner shaft 26 is slidably received within outer shaft 15. First attachment member 14 is fixedly coupled to a distal end of outer shaft 15. Inner shaft 26 extends distally beyond first attachment member 14 and is fixedly coupled to a proximal end 30 of second attachment member 16.

Figure 3:
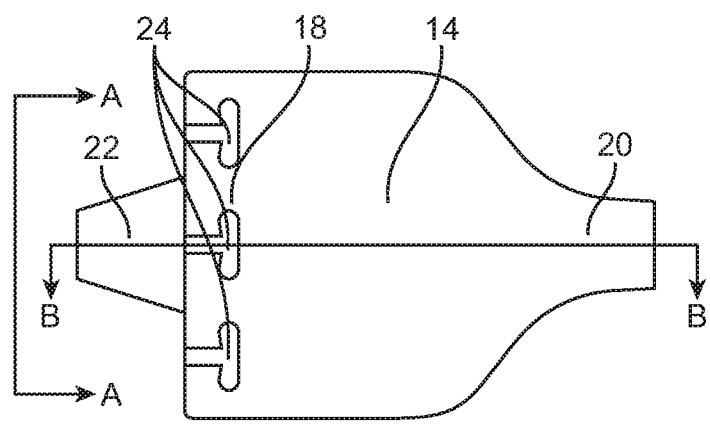
FIG. 3 is a top view of a first attachment member according to an embodiment.

As shown in FIG. 2, first attachment member 14 comprises at least one coupling portion 18 configured to selectively couple with a portion of medical device 12, for example, first end portion 46 of medical device 12 (see FIG. 6). In some embodiments, as best seen in FIG. 3, which is a top view of first attachment member 14, coupling portion 18 comprises an outer surface of first attachment member 14 that defines one or more slots 24 each configured to receive a respective coupling member of medical device 12, for example, coupling members 52 of first end portion 46 of the medical device 12 (see FIG. 6). The shape of slots 24 closely corresponds to the shape of the respective coupling member 52 of medical device 12. For example, if coupling members 52 are T-shaped, slots 24 are similarly T-shaped as shown in FIG. 3, or if coupling members 52 are paddle-shaped, slots 24 are similarly paddle-shaped.

Figure 5:
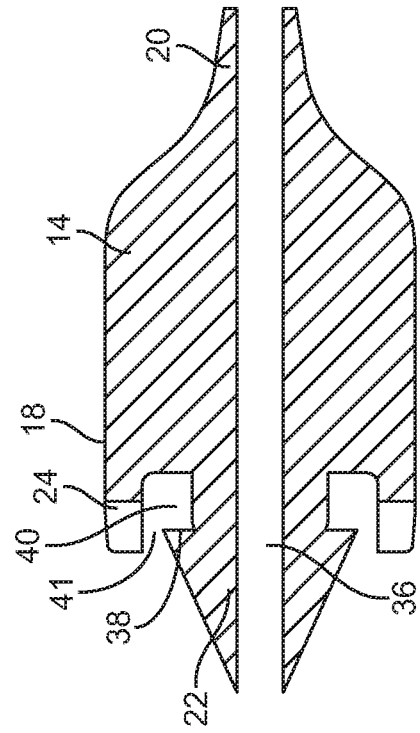
FIG. 5 is a cross-sectional view of the first attachment member of FIGS. 3 and 4 taken from line B-B in FIG. 3.
Figure 4:
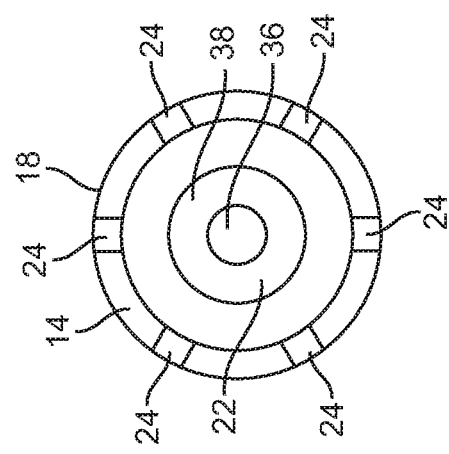
FIG. 4 is a distal view of the first attachment member of FIG. 3 taken from line A-A in FIG. 3.

Referring to FIG. 4 and FIG. 5, a view from line A-A in FIG. 3 and a cross-sectional view from line B-B in FIG. 3, respectively, first attachment member 14 defines a central lumen 36 for slidably receiving inner shaft 26. In some embodiments, the coupling portion's outer surface 18 and distal end 22 of first attachment member 14 collectively define a cavity 40. Cavity 40 is in communication with slots 24. Cavity 40 is sized to receive coupling members 52 of medical device 12 after passing through slots 24. Cavity 40 has an opening 41 that allows medical device 12 to axially extend toward second attachment member 16 when coupling members 52 are received within cavity 40. Cavity 40 can circumferentially surround first attachment member 14.

In some embodiments, distal end 22 defines a shoulder 38 that axially bounds cavity 40. Shoulder 38 can be sized and shaped to prevent coupling members 52 within cavity 40 from axially exiting cavity 40 through opening 41. In some embodiments, shoulder 38 of first attachment member 14 applies the first tensile force to medical device 12 as first attachment member 14 moves relative to second attachment member 16 to increase axial distance 17. In some embodiments, shoulder 38 is sized and shaped to apply the first tensile force directly to a radially intermediate surface of coupling members 52 of medical device 12. In some embodiments, shoulder 38 is sized and shaped to apply the first tensile force directly to an axially intermediate surface of medical device 12, for example, a distal surface of coupling members 52. When coupling members 52 of medical device 12 are within cavity 40, the coupling portion's outer surface 18 circumferentially surrounds and constrains a portion of medical device 12, for example, first portion 46, to prevent outward radially expansion of medical device 12 in self-expanding embodiments.

In some embodiments, delivery system 10 can be configured such that first attachment member 14, including outer surface 18, rotates relative to medical device 12 when coupling members 52 are within cavity 40. For example, a user can manipulate a proximal end of delivery system 10 to cause first attachment member 14 to rotates, for example, by rotating outer shaft 15. Rotation of first attachment member 14 allows a user to selectively and radially align or misalign coupling members 52 of medical device 12 with slots 24 defined by coupling portion's outer surface 18.

In some embodiments, second attachment member 16 is substantially a mirror image of first attachment member 14 as shown in FIGS. 3-5 but configured to couple to second end portion 50 and includes substantially the same features of first attachment member 14 described above. For example, as shown in FIG. 2, second attachment member 16 comprises a coupling portion 28 configured to couple to a portion of medical device 12, for example, a second end portion 50 of medical device 12. As shown in FIG. 2, coupling portion 28 comprises an outer surface that defines one or more slots 34 each configured to receive a respective coupling member 54 (see FIG. 6). The shape of slots 34 corresponds to the shape of the respective coupling members 54 of medical device 12. For example, if coupling members 54 are T-shaped, slots 34 are similarly T-shaped, or if coupling members 54 are paddle-shaped, slots 34 are similarly paddle-shaped. Second attachment member 16 also comprises a distal end 32. In some embodiments, distal end 32 forms the distal tip of delivery system 10 and can have an atraumatic shape.

FIGS. 7-12 illustrate coupling of a portion of medical device 12, for example, first end portion 46, with first attachment member 14 according to an embodiment. In some embodiments, coupling of a portion of medical device 12, for example, second end portion 50, with second attachment member 16 is a mirror image of FIGS. 7-12.

Figure 7:
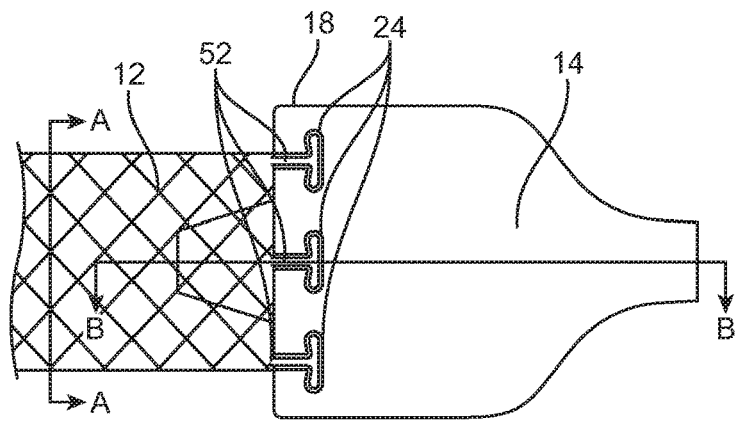
FIG. 7 is a top view of a first attachment member coupled to a first end portion of a medical device at a loading step according to an embodiment.
Figure 8:
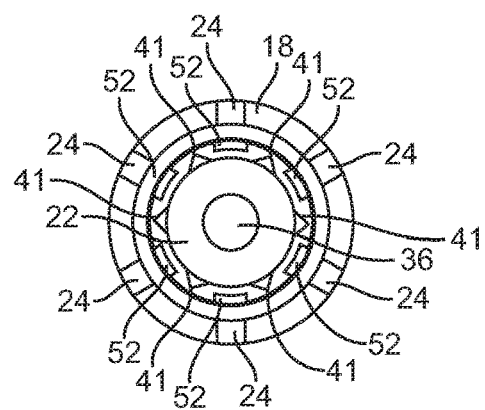
FIG. 8 is a cross-sectional view of the first attachment member coupled to the first end portion of a medical device of FIG. 7 taken from line A-A in FIG. 7.
Figure 9:
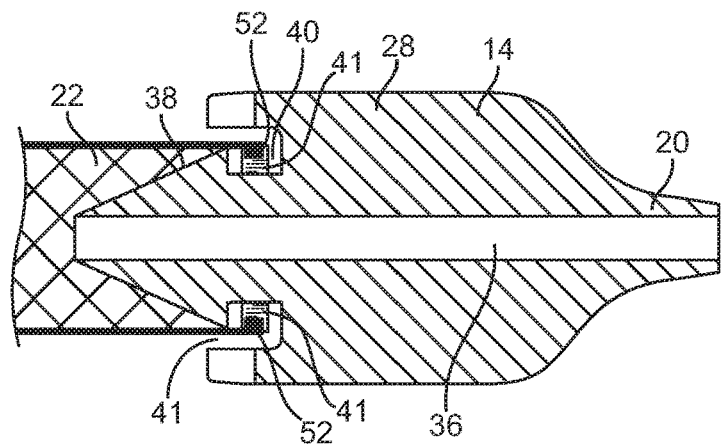
FIG. 9 is a cross-sectional view of the first attachment member coupled to the first end portion of a medical device of FIGS. 7 and 8 taken from line B-B in FIG. 7.

In FIGS. 7-9, coupling members 52 of medical device 12 are radially aligned with slots 24 defined by coupling portion's outer surface 18. First end portion 46 of medical device 12 comprising coupling members 52 is then compressed to pass coupling members 52 through slots 24 and into cavity 40 (see FIGS. 8 and 9). Shoulder 38 of first attachment member 14 prevents coupling members 52 of medical device 12 from axially exiting cavity 40 through opening 41. Shoulder 38 also applies the first tensile force to medical device 12, for example, at coupling members 52, when first attachment member 14 moves relative to second attachment member 16 to increase axial distance 17.

Figure 10:
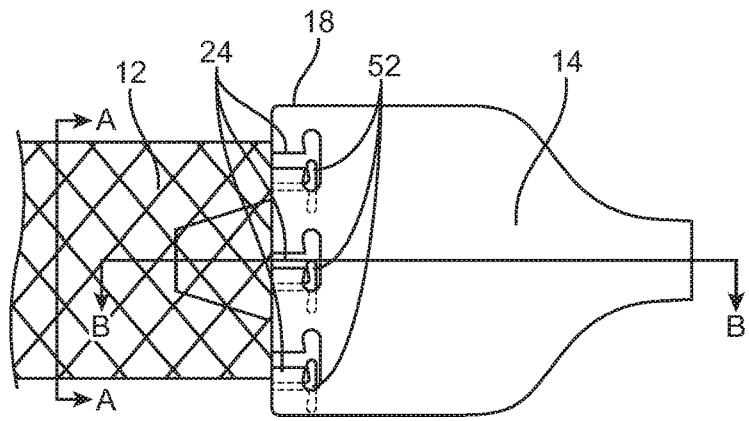
FIG. 10 is a top view of a first attachment member coupled to the first end portion of a medical device at another loading step according to an embodiment.
Figure 11:
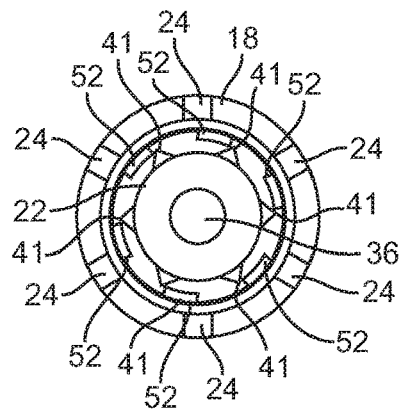
FIG. 11 is a cross-sectional view of the first attachment member coupled to the first end portion of a medical device of FIG. 10 taken from line A-A in FIG. 10.
Figure 12:
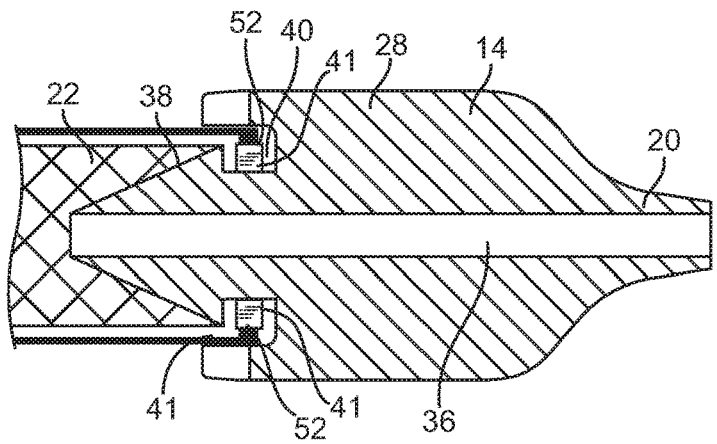
FIG. 12 is a cross-sectional view of the first attachment member coupled to the first end portion of a medical device of FIGS. 10 and 11 taken from line B-B in FIG. 10.

In FIGS. 10-12, first attachment member 14 is rotated relative to medical device 12 such that at least a portion of coupling members 52 is radially misaligned with slots 24. Accordingly, solid portions of coupling portion's outer surface 18 are radially aligned with at least portions of coupling members 52 to radially constrain the covered portion of medical device 12 and prevent outward radial expansion of at least first end portion 46 of medical device 12.

Figure 13:
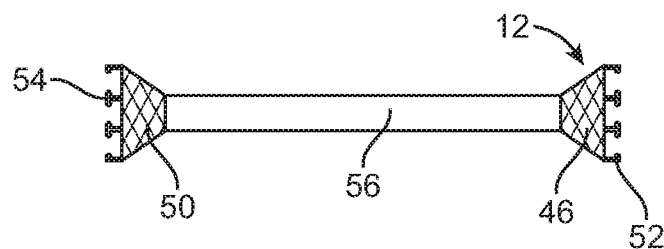
FIG. 13 is a side view of a medical device at a deployment step according to an embodiment.

Delivery system 10 facilities deployment of a medical device within a patient's body lumen or cavity. FIGS. 13-20 schematically illustrate a method of deploying medical device 12 according to an embodiment. In FIG. 13, medical device 12 is inserted within an accessory tube 56 by compressing medical device 12 to an intermediate compressed diameter. The inner dimension of accessory tube 56 is larger than the outer dimension of second attachment member 16 so that second attachment member 16 can pass through medical device 12 when inserted in accessory tube 56. Accessory tube 56 has an axial length such that first end portion 46 (including coupling members 52) of medical device 12 extends from one end of accessory tube 56, and second end portion 50 (including coupling members 54) extends from the other end of accessory tube 56. In some embodiments, medical device 12 is loaded within accessory tube 56 outside the patient.

Second attachment member 16 of delivery system 10 is then passed through the lumen of medical device 12 loaded with accessory tube 56 until first end portion 46 of medical device 12 is axially aligned with first attachment member 14 and coupling members 52 are radially aligned with slots 24 of first attachment member 14 as shown in FIG. 7.

Figure 14:
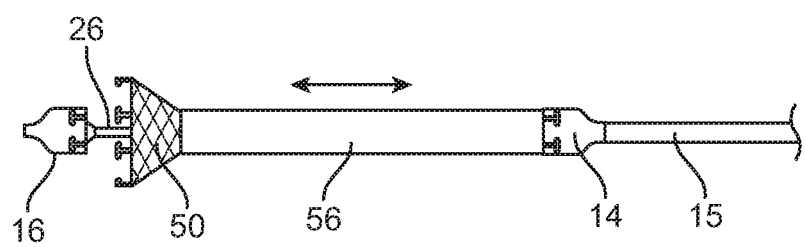
FIG. 14 is a side view of the medical device of FIG. 13 and a delivery system at a deployment step according to an embodiment.

In FIG. 14, to couple first end portion 46 of medical device 12 to first attachment member 14 of delivery system 10, accessory tube 56 is slid relative to medical device 12 in a proximal direction toward first attachment member 14 to compress first end portion 46 such that coupling members 52 pass through slots 24 of first attachment member 14 and into cavity 40. First attachment member 14 can be rotated relative to medical device 12 such that at least a portion of coupling members 52 are radially misaligned with slots 24 to radially constrain the covered portions of medical device 12 and prevent outward radial expansion of medical device 12 as shown in FIGS. 10-12.

To couple second end portion 50 of medical device 12 to second attachment member 16 of the delivery system 10, accessory tube 56 can then be slid relative to medical device 12 in a distal direction toward second attachment member 16 to compress second end portion 50 such that coupling members 54 pass through slots 34 of second attachment member 16 and into the cavity (similar to cavity 40 of first attachment member 14) defined by second attachment member 16. Second attachment member 16 can be rotated relative to medical device 12 such that at least a portion of coupling members 54 are radially misaligned with slots 34 to radially constrain the covered portions of medical device 12 and prevent outward radial expansion of medical device 12 similar to how first attachment member 14 radially constrains medical device 12 as illustrated in FIGS. 10-12.

Figure 15:
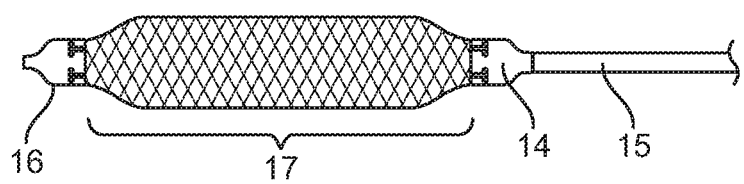
FIG. 15 is a side view of the medical device and the delivery system at another deployment step according to an embodiment.
Figure 16:
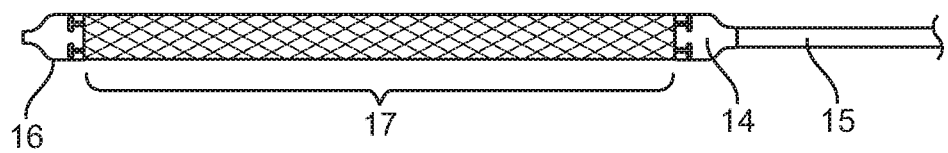
FIG. 16 is a side view of the medical device and the delivery system at another deployment step according to an embodiment.

In FIG. 15, accessory tube 56 is removed, and in FIG. 16, first attachment member 14 is moved relative to second attachment member 16 to increase distance 17 between first attachment member 14 and second attachment member 16. Increasing distance 17 causes first attachment member 14 to apply a first tensile force to first end portion 46 of medical device 12 in a first proximal direction. For example, shoulder 38 of first attachment member 14 can apply the first tensile force to medical device 12. Increasing distance 17 also causes second attachment member 16 to apply a second tensile force to second end portion 50 of medical device 12 in a second distal direction substantially opposite from the first direction. These tensile forces further compress the medical device 12 from an intermediate compressed outer dimension to a smaller compressed outer dimension.

Medical device 12 and delivery system 10 are then introduced into a body lumen or cavity and advanced to a target location, for example, location within or near the heart. In some embodiments, intermediate portion 48 of medical device 12 remains uncovered by delivery system 10 as medical device 12 is advanced to the target location.

Figure 17:
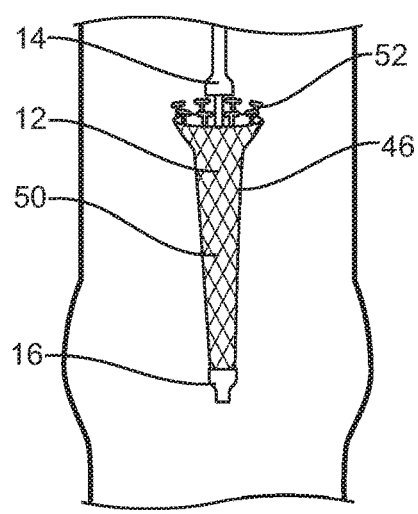
FIG. 17 is a side view of the medical device and the delivery system at another deployment step according to an embodiment.
Figure 18:
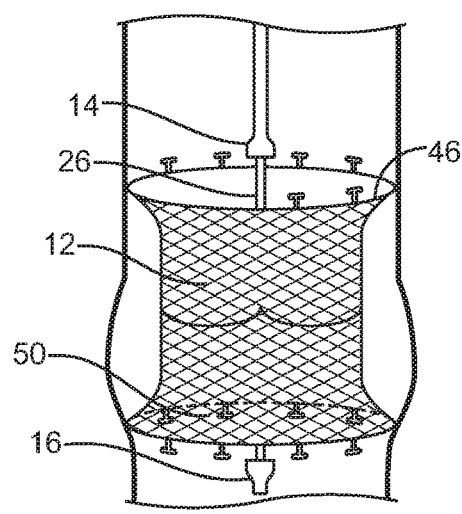
FIG. 18 is a side view of the medical device and the delivery system at another deployment step according to an embodiment.
Figure 19:
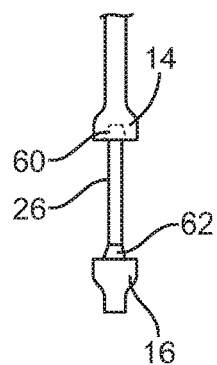
FIG. 19 is a side view of the delivery system at another deployment step according to an embodiment.
Figure 20:
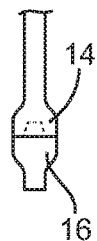
FIG. 20 is a side view of the delivery system at another deployment step according to an embodiment.

FIG. 17 illustrates medical device 12 and delivery system 10 at a target location, for example, at the aortic valve complex. At the target location, first end portion 46 of medical device 12 is decoupled from first attachment member 14, and second end portion 50 of medical device 12 is decoupled from second attachment member 16. In some embodiments, decoupling from first attachment member 14 comprises rotating first attachment member 14 relative to medical device 12 such that coupling members 52 of medical device 12 are aligned with slots 24 of first attachment member 14, allowing first end portion 46 of medical device 12 to radially expand. In some embodiments, decoupling from second attachment member 16 comprises rotating second attachment member 16 relative to medical device 12 such that coupling members 54 of medical device 12 are aligned with slots 34 of second attachment member 16, allowing second end portion 50 of medical device 12 to radially expand. FIG. 18 illustrates medical device 12 decoupled from both first and second attachment members 14 and 16 and deployed at the target location. Then, as shown in FIGS. 19 and 20, second attachment member 16 and first attachment member 14 can be moved relative to each other such that second attachment member 16 is adjacent to first attachment member 14. At this point, delivery catheter 10 can be removed from the patient anatomy.

Although in FIG. 6 first end portion 46 is the outflow portion of a valve prosthesis, in some embodiments, first end portion 46 can be the inflow portion of a valve prosthesis, and second end portion 50 can be the outflow portion of a valve prosthesis.

Embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, may need to be revisited. Further, the Examiner is also reminded that any disclaimer made in the instant application should not be read into or against the parent application.

What is claimed is:

1. A system for replacing a native heart valve of a patient, comprising:
   a prosthetic heart valve comprising a self-expanding frame and a valve assembly coupled to the self-expanding frame, the prosthetic heart valve comprising a first end portion, an intermediate portion, and a second end portion; and
   a delivery system for deploying the prosthetic heart valve, the delivery system comprising:
      a first attachment member configured to selectively couple to and radially constrain the first end portion of the prosthetic heart valve; and
      a second attachment member configured to selectively couple to and radially constrain the second end portion of the prosthetic heart valve,
   wherein the first attachment member is configured to move relative to the second attachment member such that the first attachment member applies a first tensile force to the first end portion of the prosthetic heart valve in a first direction and the second attachment member applies a second tensile force to the second end portion of the prosthetic heart valve in a second direction substantially opposite from the first direction, and
   wherein the first attachment member and the second attachment member are configured to selectively decouple from the first end portion and the second end portion, respectively, to release the prosthetic heart valve from the delivery system, thereby enabling the prosthetic heart valve to self-expand.

2. The system of claim 1,
   wherein the first end portion of the prosthetic heart valve comprises a plurality of first coupling members,
   wherein the first attachment member includes a first outer surface defining a plurality of first slots leading to a first cavity, wherein each of the plurality of first slots is configured to receive a respective one of the plurality of first coupling members, and
   wherein the first attachment member is configured to rotate between a first position wherein the first coupling members are disposed in the first cavity and the plurality of first slots are misaligned with the respective first coupling members such that the first outer surface radially constrains the first coupling members, and a second position wherein each of the plurality of first slots is radially aligned with one of the plurality of first coupling members such that each of the first coupling members may expand radially outward from the first cavity through a respective first slot.

3. The system of claim 2,
   wherein the second end portion of the prosthetic heart valve comprises a plurality of second coupling members,
   wherein the second attachment member includes a second outer surface defining a plurality of second slots leading to a second cavity, wherein each of the plurality of second slots is configured to receive a respective one of the plurality of second coupling members, and
   wherein the second attachment member is configured to rotate between a first position wherein the second coupling members are disposed in the second cavity and the plurality of second slots are misaligned with the respective second coupling members such that the second outer surface radially constrains the second coupling members, and a second position wherein each of the plurality of second slots is radially aligned with one of the plurality of second coupling members such that each of the second coupling members may expand radially outward from the second cavity through a respective second slot.

4. The system of claim 3, further comprising:
   an outer shaft coupled to the first attachment member; and
   an inner shaft disposed within the outer shaft and coupled to the second attachment member,
   wherein the inner shaft and the outer shaft are slidable relative to each other such that the outer shaft and the inner shaft are configured to be moved relative to each other in opposite directions to apply the first tensile force and the second tensile force.

5. The system of claim 4, wherein the outer shaft is configured to rotate the first attachment member between the first position and the second position, and wherein the inner shaft is configured to rotate the second attachment member between the first position and the second position.

6. The system of claim 1, further comprising:
   an outer shaft coupled to the first attachment member; and
   an inner shaft disposed within the outer shaft and coupled to the second attachment member,
   wherein the inner shaft and the outer shaft are slidable relative to each other such that the outer shaft and the inner shaft are configured to be moved relative to each other in opposite directions to apply the first tensile force and the second tensile force.

7. The system of claim 6, wherein a distal end of the outer shaft is proximal to the prosthetic heart valve, and wherein the outer shaft is an outermost shaft of the delivery system.

8. A system for replacing a native heart valve of a patient, comprising:
   a prosthetic heart valve comprising a self-expanding frame and a valve assembly coupled to the self-expanding frame, the prosthetic heart valve comprising a first end portion, an intermediate portion, and a second end portion; and a delivery system for deploying the prosthetic heart valve, the delivery system comprising:
- a first attachment member configured to selectively couple to and radially constrain the first end portion of the prosthetic heart valve;
- a second attachment member configured to selectively couple to and radially constrain the second end portion of the prosthetic heart valve,
- an outer shaft coupled to the first attachment member; and
- an inner shaft disposed within the outer shaft and coupled to the second attachment member, wherein the inner shaft and the outer shaft are slidable relative to each other such that the outer shaft and the inner shaft are configured to be moved relative to each other in opposite directions to apply a first tensile force to the first end portion of the prosthetic heart valve in a first direction and a second tensile force to the second end portion of the prosthetic heart valve in a second direction substantially opposite the first direction.

9. The system of claim 8,
wherein the first end portion of the prosthetic heart valve comprises a plurality of first coupling members,
wherein the first attachment member includes a first outer surface defining a plurality of first slots leading to a first cavity, wherein each of the plurality of first slots is configured to receive a respective one of the plurality of first coupling members, and
wherein the first attachment member is configured to rotate between a first position wherein the first coupling members are disposed in the first cavity and the plurality of first slots are misaligned with the respective first coupling members such that the first outer surface radially constrains the first coupling members, and a second position wherein each of the plurality of first slots is radially aligned with one of the plurality of first coupling members such that each of the first coupling members may expand radially outward from the first cavity through a respective first slot.

10. The system of claim 9,
wherein the second end portion of the prosthetic heart valve comprises a plurality of second coupling members,
wherein the second attachment member includes a second outer surface defining a plurality of second slots leading to a second cavity, wherein each of the plurality of second slots is configured to receive a respective one of the plurality of second coupling members, and
wherein the second attachment member is configured to rotate between a first position wherein the second coupling members are disposed in the second cavity and the plurality of second slots are misaligned with the respective second coupling members such that the second outer surface radially constrains the second coupling members, and a second position wherein each of the plurality of second slots is radially aligned with one of the plurality of second coupling members such that each of the second coupling members may expand radially outward from the second cavity through a respective second slot.

11. The system of claim 10, wherein the outer shaft is configured to rotate the first attachment member between the first position and the second position, and wherein the inner shaft is configured to rotate the second attachment member between the first position and the second position.

12. The system of claim 8, wherein a distal end of the outer shaft is proximal to the prosthetic heart valve, and wherein the outer shaft is an outermost shaft of the delivery system.

* * * * *